United States Patent [19]

Morishita et al.

[11] Patent Number: 5,146,169

[45] Date of Patent: Sep. 8, 1992

[54] REFERENCE ELECTRODE AND A PAIR OF ELECTRODES FOR DETECTING THE ACIDITY OR BASICITY OF OIL

[75] Inventors: Shinya Morishita; Kenichi Suzuki; Masae Oohori; Masahiko Nakada, all of Aichi, Japan

[73] Assignees: Kabushiki Kaisha Toyota Chuo Kenkyusho, Aichi; Toyota Jidosha Kabushiki Kaisha, Toyota, both of Japan

[21] Appl. No.: 582,425

[22] Filed: Sep. 13, 1990

[30] Foreign Application Priority Data

Sep. 13, 1989 [JP] Japan .................................. 1-237758
Dec. 28, 1989 [JP] Japan .................................. 1-340856

[51] Int. Cl.$^5$ ........................................ G01N 27/416
[52] U.S. Cl. .................................. 324/438; 324/71.1; 204/433
[58] Field of Search .............. 324/425, 438, 439, 71.1; 204/433

[56] References Cited

U.S. PATENT DOCUMENTS 4,988,418 1/1991 Beck et al. ...................... 204/433 X

OTHER PUBLICATIONS

Patent Abstracts of Japan, JP-A-56-47614, Apr. 30, 1981, "Automatic Oil Replacing Device".
Patent Abstracts of Japan, JP-A-61-259158, Nov. 17, 1986, "Method for Detecting Acidity and Basicity of Oil and Reference Electrode".
Patent Abstracts of Japan, JP-A-62-25250, Feb. 3, 1987, "Detection of Acidity and Basicity of Oil and Reference Electrode".
Patent Abstracts of Japan, JP-A-61-20851, Jan. 29, 1986, "Device for Judging Degradation of Lubrication Oil".

*Primary Examiner*—Jack B. Harvey
*Attorney, Agent, or Firm*—Oblon, Spivak, McClelland, Maier & Neustadt

[57] ABSTRACT

A reference electrode is formed of lead, zinc, tin, indium, cadmium, magnesium, or any alloy thereof. A pair of electrodes comprising the reference electrode and a responding electrode made of a conductive solid, when placed in oil, develop a potential difference varying with the acidity or basicity of the oil and thus enable the efficient determination of the acidity or basicity.

8 Claims, 4 Drawing Sheets

REFERENCE ELECTRODE AND A PAIR OF ELECTRODES FOR DETECTING THE ACIDITY OR BASICITY OF OIL

BACKGROUND OF THE INVENTION

1. Field of the Invention

This invention relates to a reference electrode and a pair of electrodes which are used for detecting the acidity or basicity of oil to detect its deterioration quickly and accurately.

2. Description of the Related Art

Various kinds of oils, such as fuel oil, a working fluid, quenching oil and lubricating oil, are used in various fields of industry. It is, however, known that these oils gradually increase their acidity due to oxidation by air, the accumulation of a combustion product, or other reasons during their storage or use and eventually undergo an undesirable reduction in corrosion resistance and other properties.

It is, therefore, a matter of great importance in the storage and maintenance of any oil to detect its deterioration quickly and accurately. In this connection, the JIS K2501 method for a test for determining the neutralization number of petroleum products has usually been employed for determining the acidity or basicity of oil. According to this method, a sample of oil is diluted with a solvent prepared by mixing toluene, isopropyl alcohol and water, and its dilution is subjected to titration analysis with a standard acid or base solution, whereby the amount of an acidic or basic substance which the oil contains is determined. This method is, however, too complicated, insofar as it is not intended for determining the acidity or basicity of oil directly. Moreover, it cannot be used for detecting a change in acidity or basicity of oil continuously.

An instrument called a pH meter is commercially available as the only device which can determine the acidity or basicity of an aqueous solution directly and continuously with a high level of reliability. The sensor portion of this instrument is so constructed as to work in accordance with an electrochemical principle, and comprises a reference electrode maintaining a constant electrode potential, and a pH electrode showing an electrode potential varying in response to the acidity or basicity of an aqueous solution. If this pair of electrodes are dipped in the aqueous solution to be examined, a potential difference which is proportional to its pH is developed between the electrodes. This potential difference is measured by a potentiometer, which the instrument contains, whereby the pH of the solution, or its acidity or basicity is determined.

A known electrode, such as a calomel or silver-silver chloride electrode, is used as the reference electrode. A known glass, antimony or oxide electrode is used as the pH electrode. The pH meter as hereinabove described can, in principle, be considered as being usable for detecting the acidity or basicity of oil. In fact, the Japanese Patent Application laid open under No. 47614/1981, for example, proposes the use of a commercially available pH meter for determining the basicity of engine oil.

The commercially available or known reference electrodes have, however, been found to be extremely low in potential stability when used in oil, apparently because of their own construction. They generally comprise an outer cylinder made of glass or a resin, an electrode forming element disposed in the outer cylinder and including an aqueous solution of a salt, and a diaphragm provided at an end of the outer cylinder, having apertures which are at least as large as, say, pinholes, and thereby defining a liquid junction between the aqueous solution in the cylinder and the liquid to be examined. If this type of reference electrode is used in oil, the contact of the aqueous solution in the cylinder with the oil through the liquid junction brings about a wrong electrode potential due to the liquid junction potential, and the mutual diffusion which proceeds between the aqueous solution and the oil with the passage of time gives rise to a substantial deviation of the electrode potential from its initial value. As a result, the electrode ceases to be of use as a reference electrode.

Moreover, no known electrode can be used at a temperature which is higher than 100° C. No known electrode can, therefore, be used for examining, for example, quenching oil having any such temperature.

An electrode relying upon an equilibrium reaction between ferrocyanide and ferricyanide ions (Japanese Patent Application laid open under No. 259158/1986) and an electrode relying upon an equilibrium reaction between lead sulfate and lead (Japanese Patent Application laid open under No. 25250/1987) have been proposed as the reference electrodes which can overcome the drawbacks of the older known electrodes and be used in oil. These electrodes are, however, of the type in which the substances for developing a reference potential are carried on the substrate material. Therefore, they have been found to lack reliability for a long period of use in oil, as those substances are very likely to drop off the substrate material when the electrodes are used in an environment in which the industrial use of oil is usually made, for example, when they are used in a flow of oil, or in a place where mechanical vibration occurs.

The known pH-response electrodes made of e.g. glass are complicated in construction and yet are easily broken during use. There are also known electrodes made of metals, such as stainless steel, and having a passive oxide film formed thereon by oxidation in the air. This passive film, however, has an undesirably small and varying thickness which brings about an undesirably great variation in the results of potential determination.

SUMMARY OF THE INVENTION

It is a basic object of this invention to provide a reference electrode and a pair of electrodes including the reference electrode which can overcome the drawbacks of the known electrodes as hereinabove pointed out and be used for detecting the acidity or basicity of oil reliably for a long period of time.

According to this invention, there is provided a reference electrode for use with another electrode capable of responding to the acidity or basicity of oil and thereby developing a varying potential difference, the reference electrode being made of a metallic material selected from among lead, zinc, tin, indium, cadmium and magnesium, and alloys thereof.

The reference electrode of this invention is made of a metal or alloy itself, as opposed to the known electrode carrying on its surface a substance used for developing a reference potential. Therefore, it is free from the problem which has hereinabove been pointed out as arising from the use of any such known electrode in the environment where mechanical vibration acts upon it, or a flow of oil exists, and can be used in oil reliably for a long period of time.

While no detail is known of the mechanism which enables the reference electrode of this invention to maintain a constant potential in oil, the following is a description of the principle which is assumed to be relevant:

The metal of which the electrode is made is a base metal and at the anode, it is slowly dissolved in oil as shown below by way of example:

$$Pb \rightarrow Pb^{2+} + 2e^- \tag{1}$$

Cathode reactions are considered to take place on the metal, as shown below:

$$2H^+ + 2e^- \rightarrow H_2 \uparrow \tag{2}$$

$$O_2 + 2H_2O + 4e^- \rightarrow 4OH^- \tag{3}$$

It is, however, considered that the presence of a high hydrogen overvoltage prevents the reaction (2) from making any substantial progress. It is also considered that the progress of the reaction (3) is very slow, since the amount of oxygen dissolved in oil is as small as only several parts per million and it is the motion of oxygen that determines the rate of the reaction. The anode reaction corresponding to the dissolution of the metal primarily has nothing to do with the acidity or basicity of oil, and the electrode potential which depends on the equilibrium of the reaction has nothing to do with the acidity or basicity of oil, either. It is apparently for these reasons that the reference electrode of this invention exhibits a constant potential when used in oil.

The electrode is easy to manufacture and handle, as it is simple in construction.

According to one aspect of this invention, there are provided a pair of electrodes which consist of a reference electrode made of a metallic material selected from among lead, zinc, tin, indium, cadmium and magnesium, and alloys thereof, and a conductive solid electrode as a responding electrode which responds to the acidity or basicity of oil and thereby shows a correspondingly varying potential.

As it is made of a conductive solid, the responding electrode for the pair of electrodes of this invention is simple in construction and is, thus, an improvement over any known pH-response electrode of glass or other material that is complicated in construction and is easily broken. It is also an improvement over any known metal electrode carrying a passive film having a varying thickness. As it has no such film, it does not show any potential fluctuation that has hitherto been caused by the variation in film thickness.

The pair of electrodes of this invention develop a large potential difference in response to any change in the pH of oil and thereby enables the quick and accurate determination of its acidity or basicity. Moreover, they are easy to manufacture and handle, as it is simple in construction.

These and other objects, features and advantages of this invention will become more apparent from the following description and the accompanying drawings.

DETAILED DESCRIPTION OF THE INVENTION

Figure 1:
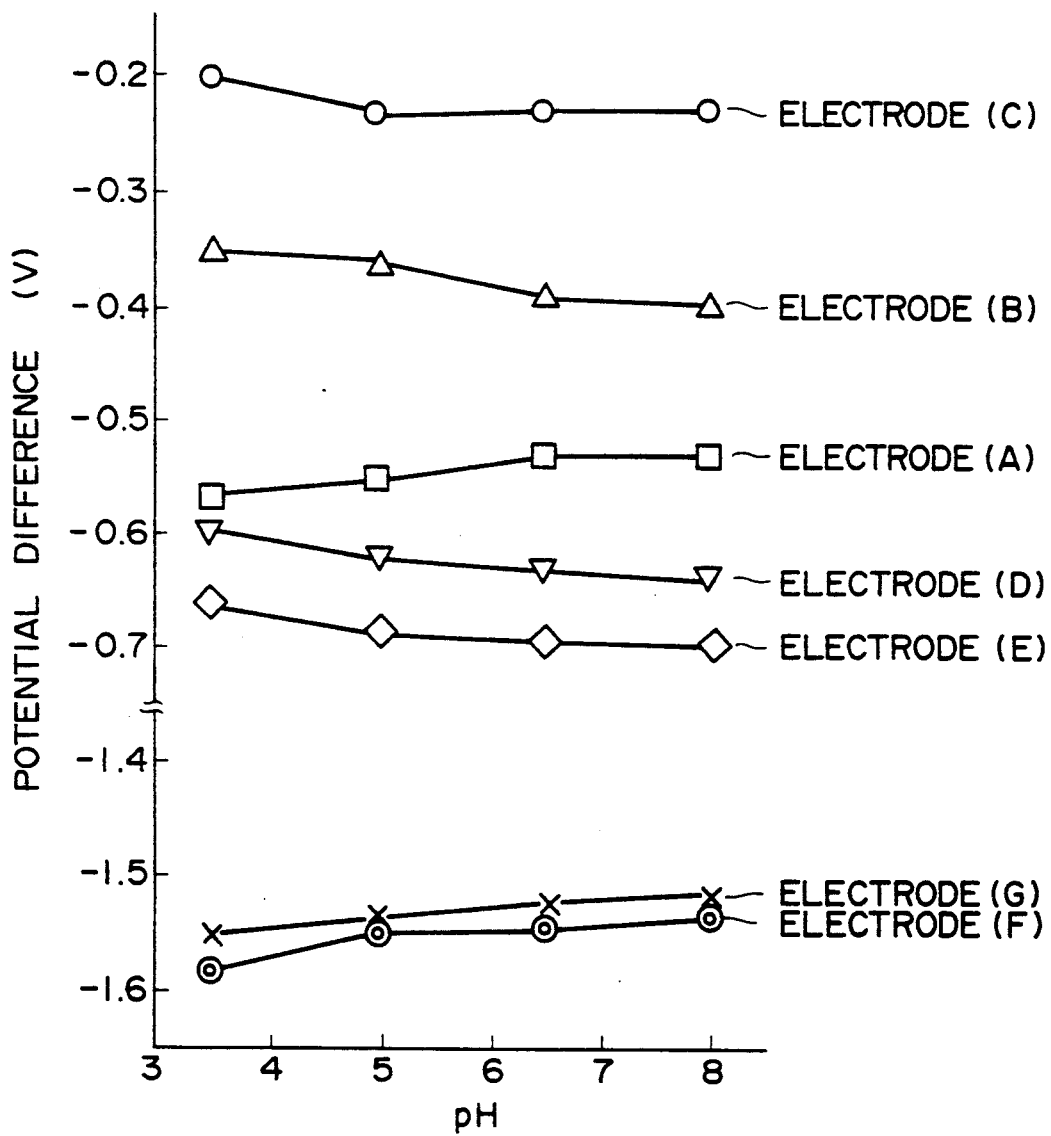
FIG. 1 is a graph showing the characteristics of reference electrodes according to EXAMPLE 1 of this invention when used with a known saturated calomel electrode as a standard.

The reference electrode according to this invention is primarily an electrode which can maintain a constant electrode potential without responding to the acidity or basicity of oil. Even an electrode having the property of responding to the acidity or basicity of oil is, however, acceptable as the reference electrode in the context of this invention if its response to the acidity or basicity of oil is very low, as compared with that of the responding electrode with which it may form the pair of electrodes according to this invention. An electrode made of tin, zinc, indium or cadmium, or an alloy thereof is acceptable as such. An electrode made of lead or magnesium, or an alloy thereof exhibits response characteristics represented by a line having an inclination which is reverse to that of the line representing the response characteristics of the responding electrode, i.e. its potential variation with the pH of oil. This type of electrode is rather desirable for use as a reference electrode, since its combination with the responding electrode enables the development of a large potential difference.

The reference electrode is made of one of the metals or alloys as hereinabove stated. It can be made by any method, such as casting or rolling. It may be shaped as a plate, rod, pipe or net, or may be formed in any other shape, if it has an appropriate surface area. The appropriate surface area of the electrode depends on the condition of the oil to be examined, the mode of arrangement of the electrode and the method of detecting the electrode potential, but is usually from 1 to 20 cm². Although there is no particular limitation to the thickness of the electrode, a thickness of at least, say, 0.5 mm is preferred if its dimensional stability and the possibility of its wear by e.g. corrosion are taken into consideration.

The reference electrode of this invention always exhibits a constant potential in oil, or a substantially constant potential, as it shows no response, or only a very low response, to the acidity or basicity of the oil.

The conductive solid electrode for the pair of electrodes according to one aspect of this invention can be made of any material having such a level of conductivity that the potential of the electrode placed in oil can be detected, i.e. the electromotive force which occurs between it and the reference electrode can be detected by an external circuit. Therefore, it can be made of not only a conductive material, such as a metal or carbon, but also a semiconductor, such as silicon.

Even an oxide or nitride film which is usually classified as an insulator can also be used if its thickness sufficiently small to permit the detection of the electrode potential. More specifically, it is possible to use, for example, a thin film electrode carrying a film of silicon nitride or aluminum oxide having a thickness of 0.1 micron or more on a metallic substrate. For detecting the potential of such an electrode, it is sufficient to use an ordinary potentiometer having an input impedance of, say, $10^{11}$ ohms.

It is generally known that the conductive solid electrode which has been exposed to the air has a large number of hydroxyl groups on its surface, and that when it is dipped in the oil to be examined, an equilibrium as shown at (4) below is established between the hydroxyl groups and the hydrogen ions which determine the acidity or basicity of the oil. Accordingly, the metallic electrode having an oxide film on its surface exhibits a potential reflecting the acidity or basicity of the oil.

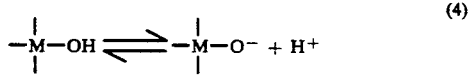
(4)

The conductive solid electrode having a clean surface not carrying a sufficiently large number of hydroxyl groups is sometimes likely to show a somewhat unstable potential immediately after it has been dipped in the oil to be examined, but as its surface is wetted with the oil and acquires a sufficiently large number of hydroxyl groups, its potential is stabilized.

A metallic electrode having an oxide film on its surface is often used as the conductive solid electrode. The metallic electrode can be made of any metal or alloy that permits the formation of a dense and stable oxide film thereon. Therefore, it can be made of, for example, stainless steel, nickel, titanium, niobium, tantalum, zirconium, or aluminum.

The oxide film preferably has a thickness of at least 0.1 micron. A film having a thickness which is smaller than 0.1 micron is likely to result in an unreliable electrode giving an undesirably fluctuating potential difference. A film having a thickness which is as large as 1.0 micron or more is also acceptable, but has the disadvantages of taking an undesirably long time for its formation, and peeling off easily.

The metallic electrode used as the responding electrode is preferably made of stainless steel, as it is less expensive and easier to work than any other material. Description will, therefore, be made in detail of a stainless steel electrode having an oxide film on its surface.

Stainless steel of any sort can be used if it permits the formation of an oxide film having a thickness of, say, 0.1 to 1.0 micron on its surface and remains chemically stable for a long period of time as an electrode. Specific examples of the stainless steels which can be employed are SUS 430, SUS 304 and SUS 316 as designated by JIS.

The electrode preferably has a surface area which is equal to that of the reference electrode. It may be formed as a lump, plate, pipe or net, or in any other shape, as far as it is positioned opposite to the reference electrode with an appropriate space therebetween.

A passive film of less than 0.1 micron in thickness is formed on stainless steel if it is left to stand in the air. This film is, however, too thin to ensure that any fluctuation in potential difference be kept within a practically permissible range. Therefore, it is necessary to form an appropriately thick oxide film having a thickness of at least 0.1 micron. A number of methods can be employed for that purpose, as will hereinafter be described.

According to a first method, a stainless steel electrode which has been degreased and rinsed with deionized water is held at a temperature of 400° C. to 500° C. for a period of 30 to 60 minutes in the air. This method enables the formation of a uniform oxide film on the whole surface of even a stainless steel electrode having a complicated shape.

According to a second method, a stainless steel electrode which has been degreased and rinsed with deionized water is dipped in a solution having a chromic anhydride concentration of 1.0 to 3.0 M and a sulfuric acid concentration of 3.5 to 5.5 M and kept at a temperature of 40° C. to 80° C. The dipping time can be shortened if the chromic anhydride or sulfuric acid concentration of the solution is increased, or if its temperature is raised. A period of 20 to 30 minutes is, for example, preferred if the solution has a chromic anhydride concentration of 2.5 M, and a sulfuric acid concentration of 5.0 M and a temperature of 70° C. The thickness of the oxide film which is formed by this treatment depends largely on the temperature of the solution. It is, therefore, important to maintain a uniform temperature throughout the solution by stirring it carefully in order to form an oxide film having a uniform thickness on a stainless steel electrode having a complicated shape.

According to a third method, a stainless steel electrode which has been degreased and rinsed with deionized water is dipped in a sodium hydroxide solution having a concentration of at least 2 M, preferably 10 M, and an electric charge of at least 0.2 $C/cm^2$ is applied while a potential difference of $-0.05$ to $+0.48$ V is maintained relative to a mercury oxide electrode in the solution having a concentration of 10 M. The proper positioning of the counter electrode is important for forming an oxide film having a uniform thickness, as its current density has a significant bearing on the thickness of the film which is formed. This method is preferably applied to a stainless steel electrode having a simple shape.

The oxide film having a thickness of about 0.1 to 1.0 micron which has been formed on the surface of stainless steel by any of the methods as hereinabove described adheres strongly to it and does not easily peel off. Moreover, it has a very high level of chemical stability to oil. Therefore, the stainless steel electrode having such an oxide film retains high response characteristics to the acidity or basicity of oil for a long period of time.

Description will now be made of a nickel, titanium, niobium, tantalum or zirconium electrode having an oxide film on its surface. Whichever of these metals may be employed, it is advisable to use a metal having a purity of at least 99% to ensure the preparation of an electrode having an oxide film of about 0.1 to 1.0 micron in thickness formed on its surface and retaining high chemical stability for a long period of time. The electrode preferably has a surface area equal to that of the reference electrode with which it forms the pair of electrodes according to one aspect of this invention. It may be formed as a lump, plate, pipe or net, or in any other shape if it can be positioned opposite to the reference electrode with an appropriate space therebetween. Various methods can be employed for forming the oxide film. A few examples thereof will hereinafter be described.

According to a first method, a nickel, titanium, niobium, tantalum or zirconium electrode which has been degreased and rinsed with deionized water is intensely heated by the oxidizing flame of a gas burner in the air for a period of several to about 20 minutes. This method can form a uniform oxide film on the whole surface of even an electrode having a complicated shape.

According to a second method, which is applicable to a titanium, niobium, tantalum or zirconium electrode, the electrode which has been degreased and rinsed with deionized water is dipped in a solution of an alkali metal hydroxide, such as lithium, sodium or potassium hydroxide, having a concentration of 0.1 to 10 M and a temperature of 20° C. to 80° C., and a voltage of 10 to 200 V, preferably 50 to 100 V, is applied to the counter electrode in the solution. If the application of an electric current is continued for a period of at least 10 minutes, preferably at least 30 minutes, it is possible to form a uniform oxide film on the whole surface of even an electrode having a complicated shape, as the applied current, on which the rate of formation of the film depends, tends to be concentrated on those portions of the film being formed which are smaller in thickness than the rest thereof.

At this moment, it is still difficult to determine directly the specific values of potentials which are developed on the reference and responding electrodes forming the pair of electrodes according to the one aspect of this invention when they are placed in oil. It is, however, possible to determine the approximate values experimentally.

Description will now be made of the use of the pair of electrodes according to this invention, which consist of a reference electrode made of a material selected from among lead, zinc, tin, indium, cadmium and magnesium, and alloys thereof, and a responding electrode made of a specific metal or alloy, having an oxide film formed on its surface as a conductive solid, and showing a potential varying with the acidity or basicity of oil.

The pair of electrodes are dipped in the oil to be examined and the potential difference which has been developed between the two electrodes is measured by a potentiometer, as when any known pH meter is employed. In this connection, it is necessary to use a potentiometer having a high input impedance, as one which is used when any known reference electrode is employed, so that the passage of an electric current through the related circuit may be avoided as far as possible.

The acidity or basicity of the oil under examination can be determined if the potential difference which has been measured is compared with a calibration curve showing the relation between the potential difference and the acidity or basicity of the same kind of oil as the oil under examination based on the results of a series of preliminary measurements. As the potential difference is proportional to the acidity or basicity of oil, it is easy to determine the acidity or basicity of any kind of oil directly from the potential difference if an appropriate calibration curve is ready for use. It is also possible to determine any change in the acidity or basicity of oil with the passage of time if a change in potential difference is appropriately detected.

The pair of electrodes according to this invention are so stable to heat as to be suitable for use not only at normal temperature, but also at an elevated temperature which is as high as, say, 100° C. or above.

There is every likelihood that the oil to be examined may contain a small amount of water as a result of absorbing moisture, or for any other reason. Such water is, however, virtually unlikely to have any adverse effect on the pair of electrodes of this invention if it is soluble with the oil. More specifically, the performance of the pair of electrodes is hardly affected, even if it may be used in, for example, lubricating oil for an internal combustion engine which contains, say, 0.05 to 1.0% by weight of water.

The prolonged use of the pair of electrodes in oil is sometimes likely to bring about a gradual drop in the value of the potential difference which is detected between the electrodes. This is apparently due to the fact that the surfaces of the electrodes are inactivated to some extent or other by, for example, the adherence of the contaminants which oil contains, and thereby cause a deviation of the potentials from the normal values. The deterioration of the pair of electrodes can be rectified if a voltage which is higher than the potential difference as detected between the electrodes is applied between the electrodes from an external source without changing their polarity.

As to the polarity of the voltage which is applied from an external source to restore the pair of electrodes from its deterioration, it is important to ensure that no change occur to the polarity of the potential difference which is detected by the pair of electrodes. If the polarity is reversed, no restoring effect can be obtained. While there is no limitation as to the magnitude of the voltage which is applied, except that it need be higher than the potential difference which is normally detected between the electrodes, it is usually not necessary to apply any voltage exceeding 3 V greatly, since the potential difference which is normally produced between the electrodes forming the pair of electrodes according to this invention is expected to fall within 3 V. Although the length of time for which such voltage application is continued may depend on the degree of deterioration of the pair of electrodes, it is preferably continued for as long a period of time as possible. It can even be started immediately after the detection of the potential difference by the pair of electrodes, and continued until the next detection is made.

No detail is known of the mechanism which enables the restoration of the pair of electrodes from its deterioration when such voltage application is made, but it is probably similar to what occurs when a cell is charged. The pair of electrodes which have been dipped in oil are considered as forming a kind of cell, though no large current can be passed therethrough, and the inactivated surfaces of the electrodes bring about a drop in electromotive force, or potential difference. If a higher voltage is applied between the electrodes without changing their polarity, it is considered to reactivate the electrodes and allow the pair of electrodes to restore the original electromotive force, or potential difference, as when a cell is charged.

The invention will now be described in further detail with reference to some examples thereof.

EXAMPLE 1

Reference electrodes were prepared by using a lead electrode (A), a tin electrode (B), an indium electrode (C), a cadmium electrode (D), a zinc electrode (E), a magnesium electrode (F) and a magnesium alloy (JIS AZ61) electrode (G) each measuring 5 cm in length, 3 cm in width and 2 mm in thickness and having a purity of at least 99.9%, and by cleaning each of them with dilute nitric acid, rinsing it with water, and drying it.

Responding electrodes were prepared by using a carbon steel (JIS S45C) electrode (H) having a length of 5 cm, a width of 3 cm and a thickness of 2 mm, a glassy carbon electrode (I) having a length of 5 cm, a width of 3 cm and a thickness of 1 mm and a p-type silicon electrode (J) having a length of 5 cm, a width of 3 cm and a thickness of 0.5 mm, and by cleaning the surface of each of them with an organic solvent, and drying it.

Two more responding electrodes were prepared by using two sheets of stainless steel (SUS 304L) which were equal in dimensions to the carbon steel electrode, and by dipping them in 1000 ml of an oxidizing solution obtained by dissolving 250 g of chromic anhydride ($CrO_3$) designated as a Special Grade reagent and 500 g of sulfuric acid ($H_2SO_4$) in distilled water, heated to 70° C. and kept under stirring, removing them from the solution after 20 minutes, rinsing them with water, and drying them. The stainless steel electrodes, (K) and (L), were each found to carry a strongly adhering oxide film having a thickness of 0.3 micron on its surface. Still more responding electrodes were prepared by using a nickel electrode (M), a titanium electrode (N), a niobium electrode (O), a tantalum electrode (P) and a zirconium electrode (Q), which were of the same dimensions and purity, and by degreasing them, rinsing them with water, and heating them intensely in the oxidizing flame of a gas burner for 10 minutes, whereby a strongly adhering oxide film having a thickness of 0.2 to 1.0 microns was formed on the surface of each electrode.

The electrodes (A) to (Q) were each evaluated for its performance as a reference or responding electrode for determining the acidity or basicity of oil. They were dipped in lubricating oils for a gasoline engine having different degrees of deterioration. After three days, each oil was diluted to 25 times as large a volume with a mixed solvent consisting of equal proportions of toluene and 2-propanol. The pH of the oil was determined by a pH meter. The potential difference of each electrode was measured in combination with a known saturated calomel electrode used as a standard. The potential difference was measured at room temperature by a potentiometer having an input impedance of at least $10^{11}$ ohms. The potential differences were plotted against the pH values of the oils measured by a pH meter. The results are shown in FIGS. 1 and 2.

Figure 2:
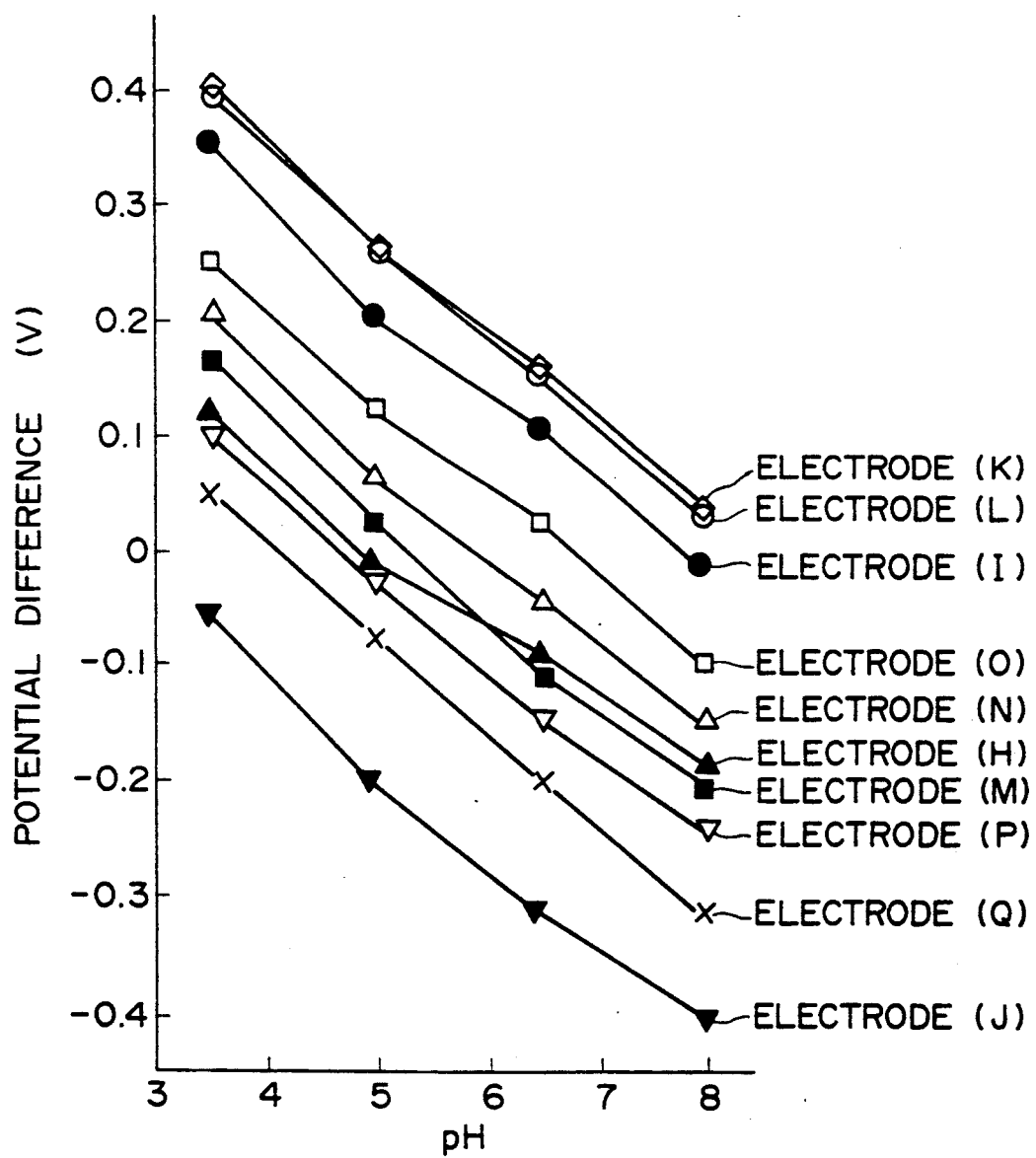
FIG. 2 is a graphs showing the characteristics of pH-response electrodes according to EXAMPLE 1 of this invention when used with a known saturated calomel electrode as a standard.

As is obvious from FIG. 1, the lead electrode (A) showed a substantially constant potential difference having a variation of only within 20 mV irrespective of the pH of the oil, and was, therefore, concluded as being more than satisfactory for use as a reference electrode.

The tin, indium, cadmium and zinc electrodes (B) to (E) showed a greater variation in potential difference with the pH of the oil in the range below 6, but since the variation was within 60 mV, every electrode was concluded as being satisfactory as a reference electrode.

The magnesium electrode (F) showed a variation in potential difference with the pH of the oil which had an inclination opposite that of the variation observed with the electrodes (B) to (E), but since the variation was smaller, it was concluded as providing a satisfactory reference electrode. The magnesium alloy electrode (G) was concluded as being comparable to the magnesium electrode (F).

All of these reference electrodes could be used for a long period of time without showing any change in characteristics, as every electrode was made of a metal or alloy itself.

All of the conductive solid electrodes (H) to (Q) showed a sharp change in potential difference with the pH of the oil, as shown in FIG. 2, and were concluded as providing excellent responding electrodes. The stainless steel electrodes (K) and (L) each having an oxide film formed thereon were both found stable and reliable as responding electrodes with a difference in characteristics of only several millivolts therebetween. Moreover, the prolonged use of any of these electrodes did not bring about any change in its characteristics.

EXAMPLE 2

The lead electrode (A) and the stainless steel electrode (K) having an oxide film were used to form a pair of electrodes. The pair of electrodes were tested for determining the acidity or basicity of eight samples of lubricating oil for a gasoline engine, i.e. a sample of new oil and seven samples of used oil produced by different manufacturers and having different grades. The electrodes (A) and (K) were dipped in each sample of oil with a distance of 1 mm therebetween and the potential difference which had been developed between the electrodes was measured by the potentiometer as hereinbefore described, while the oil was kept at a temperature of 90° C. Each sample of oil was diluted to 25 times as large a volume with a mixed solvent consisting of equal proportions of toluene and 2-propanol and its pH was determined by a pH meter, while its total base number was determined by titration analysis by the JIS K2501 method.

The potential differences as measured between the electrodes were plotted against the pH values as determined of the diluted samples of oil, and the total base numbers thereof, respectively. The relation between the potential differences and the pH values is shown by a solid line in FIG. 3, and the relation between the potential differences and the total base numbers in FIG. 4. As is obvious from the solid line in FIG. 3 and FIG. 4, the potential differences were very closely related to the pH values and the total base numbers, respectively. These results confirm that the acidity or basicity of every sample of oil was directly determined by the pair of electrodes embodying this invention.

Figure 3:
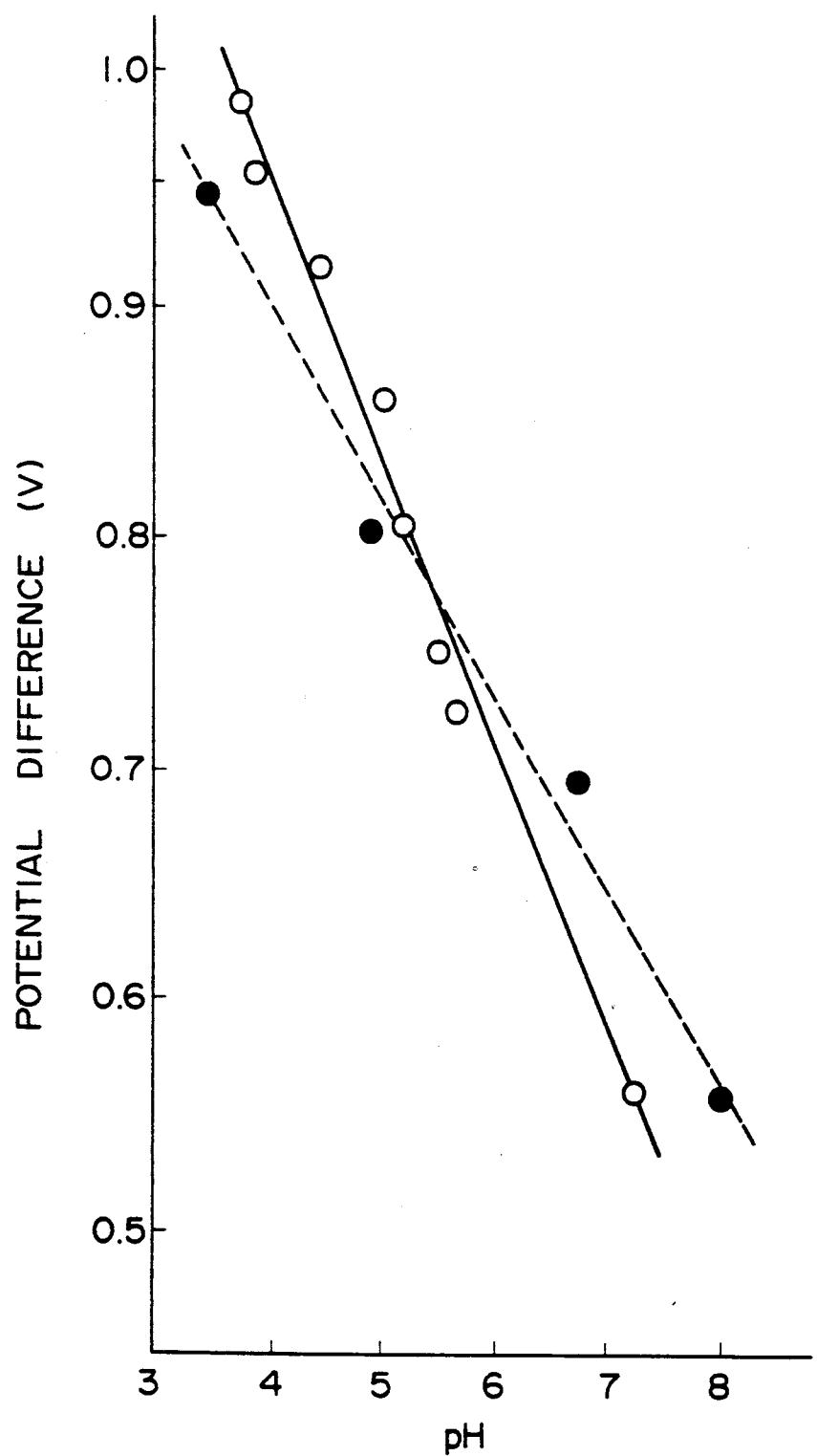
FIGS. 3 and 4 are graphs showing the characteristics of a pair of electrodes according to EXAMPLE 2 of this invention as used for the evaluation of lubricating oil for a gasoline engine.
Figure 4:
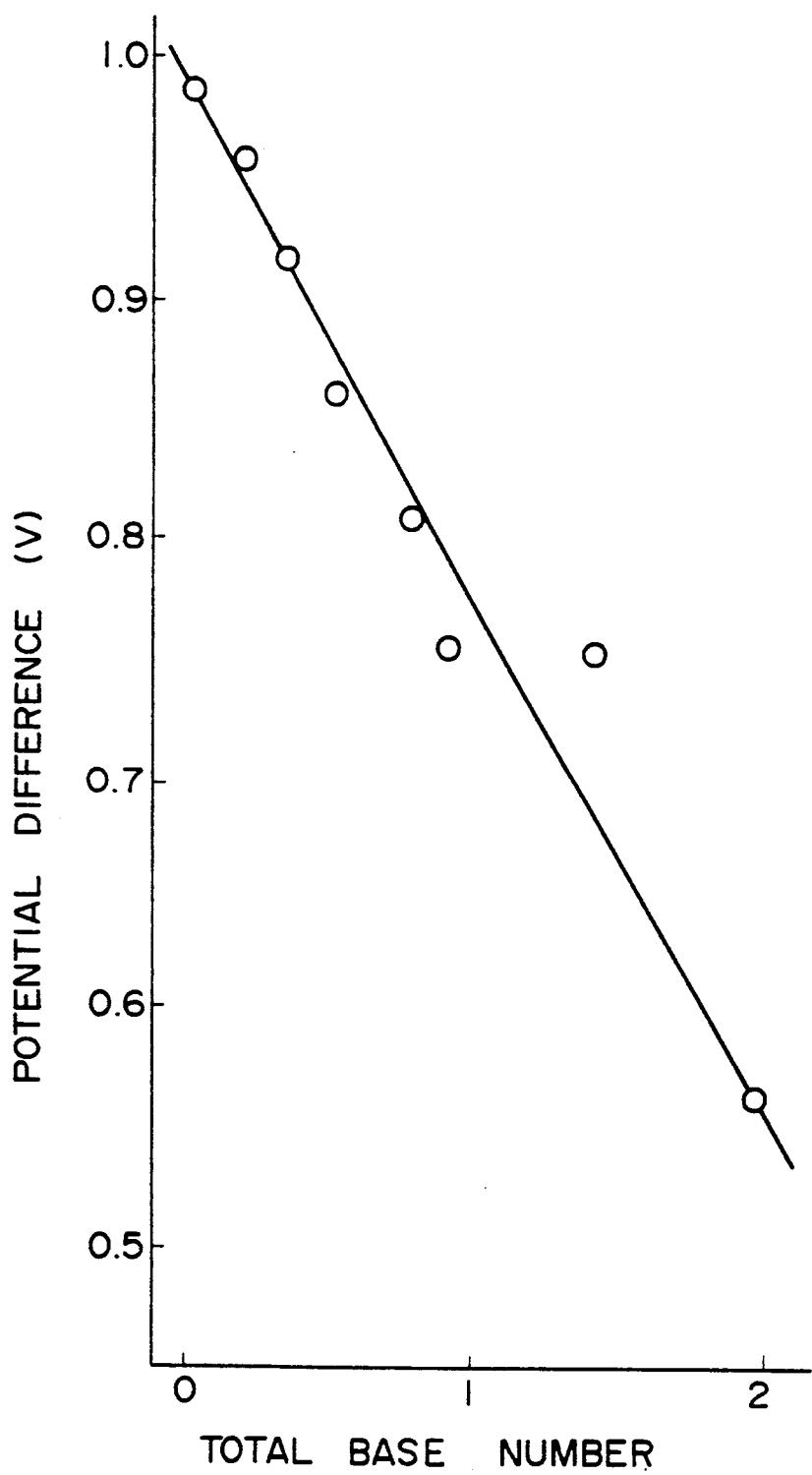

The broken line in FIG. 3 shows in relation to the pH of oil the arithmetic difference of the potential differences as measured between the reference electrode embodying this invention and the known saturated calomel electrode and between the responding electrode embodying this invention and the known saturated calomel electrode, and shown in FIGS. 1 and 2, respectively. The solid line in FIG. 3 represents a greater change in potential difference with the pH of oil than the broken line does. The pair of electrodes embodying this invention was, therefore, concluded as exhibiting better characteristics than the potential characteristics of the individual electrodes and showing a higher response to any change in acidity of oil. The excellent performance of the pair of electrodes was confirmed in the determination of the basicity of oil, too.

Similar results were obtained with all of the pair of electrodes which had been formed by employing different combinations of the electrodes according to EXAMPLE 1.

All of the pair of electrodes embodying this invention were found to retain substantially the same characteristics even after a long time of use.

EXAMPLE 3

In EXAMPLE 2, the pair of electrodes showed a potential difference of 0.955 V in the used oil having a pH of 3.9. After the pair of electrodes had been left to stand in the oil for about a month, the potential difference was measured again and was found to have dropped to 0.870 V. A voltage of 0.960 V was applied from an external source to the pair of electrodes for eight hours without changing the polarity, and the potential difference was measured again. It was 0.950 V and it follows that the pair of electrodes were restored from its deterioration substantially completely. After it had been left to stand in the oil again, a voltage of 0.900 V was applied to the pair of electrodes without changing the polarity thereof, and a voltage of 0.960 V by changing the polarity, and the potential differences were measured. No restoration had, however, been achieved in either case.

What is claimed is:

1. A pair of electrodes for detecting the acidity or basicity of oil in which a potential difference varies in response to the acidity or basicity of oil, comprising a reference electrode exhibiting no or little potential change in response to the acidity or basicity of oil and a responding electrode exhibiting potential change in response to the acidity or basicity of oil, said reference electrode being a metallic electrode formed of a base metal material selected from the group consisting of lead, zinc, tin, indium, cadmium, magnesium and an alloy thereof, and said responding electrode being a conductive solid electrode of a base metal material which is different from that of said reference electrode.

2. The pair of electrodes according to claim 1, wherein said conductive solid electrode has such a conductivity that an electromotive force between said conductive solid electrode and said reference electrode is detected by an external circuit.

3. The pair of electrodes according to claim 1, wherein said conductive solid electrode is formed of at least one material selected from the group consisting of a metal, carbon and a semiconductor.

4. The pair of electrodes according to claim 1, wherein said conductive solid electrode is formed of a metallic substrate with at least one of an oxide film and a nitride film formed thereon.

5. The pair of electrodes according to claim 4, wherein said oxide film and said nitride film have a thickness of at least 0.1 micron.

6. The pair of electrodes according to claim 4, wherein said metallic substrate is formed of at least one material selected from the group consisting of stainless steel, nickel, titanium, niobium, tantalum, zirconium and an alloy thereof.

7. The pair of electrodes according to claim 1, wherein said metallic electrode if formed of a material selected from the group consisting of lead, magnesium and an alloy thereof, said metallic electrode having a relationship between pH and the potential difference with an inclination opposite to that of the relationship in said responding electrode.

8. A method for detecting the acidity or basicity of oil in which a potential difference varies in response to the acidity or basicity of oil, comprising:

measuring the potential difference developed between a reference electrode and a responding electrode, wherein said reference electrode is a metallic electrode formed of a base metal material selected from the group consisting of lead, zinc, tin, indium, cadmium, magnesium and an alloy thereof;

wherein said reference electrode exhibits little or no potential change in response to the acidity or basicity of oil; and wherein said responding electrode is a conductive solid electrode of a base metal material which is different from that of said reference electrode.

* * * * *